United States Patent [19]

Mueller

[11] 4,450,575
[45] May 22, 1984

[54] X-RAY TOMOGRAPHY TABLE HAVING A VIRTUAL FULCRUM ARM PIVOT

[75] Inventor: Robert J. Mueller, Brookfield, Wis.

[73] Assignee: General Electric Company, Schenectady, N.Y.

[21] Appl. No.: 458,608

[22] Filed: Jan. 17, 1983

[51] Int. Cl.³ .............................................. A61B 6/02
[52] U.S. Cl. ..................................... 378/26; 378/197
[58] Field of Search ...................... 378/21, 22, 25, 26, 378/23, 24, 27, 197

[56] References Cited

U.S. PATENT DOCUMENTS

| | | | |
|---|---|---|---|
| 3,733,487 | 5/1973 | Louche et al. | 378/26 |
| 3,838,287 | 9/1974 | Barrett et al. | 378/26 |
| 4,087,694 | 5/1978 | Hellstrom et al. | |
| 4,095,110 | 6/1978 | Bunch. | |
| 4,315,156 | 2/1982 | Sell. | |

Primary Examiner—Alfred E. Smith
Assistant Examiner—T. N. Grigsby
Attorney, Agent, or Firm—Fuller, House & Hohenfeldt

[57] ABSTRACT

X-ray apparatus for tomography and other procedures. For tomography, a column is translated longitudinally parallel to the patient supporting table top. An x-ray tube is supported on the column above the table top for angulating about a laterally extending axis at a constant elevation on the column. A bucky carriage for containing a film is mounted under the top for moving longitudinally. A fulcrum arm is pivotally connected at one end directly to the bucky carriage for pivoting on a laterally extending axis lying on the film plane. The other or upper end of the arm is connected to the x-ray tube for angulating it so the central ray of the x-ray beam is always directed to the center of the film during column translation. The upper end of the fulcrum arm is slidable relative to the x-ray tube angulation axis. An extensible and contractible link means below the bucky carriage pivotally connects at its upper end to the carriage and at its lower end to the column for swinging about a lateral axis that is vertically aligned with the x-ray tube axis. The link means pivots about a lateral axis on a support member whose elevation is adjustable relative to the film plane. The elevation of the link means pivot determines the height above the taple top of a fixed vertical axis about which the fulcrum arm swings and, hence, it determines the height of the plane in a body lying on the table top that will be imaged without blurring on the film.

9 Claims, 9 Drawing Figures

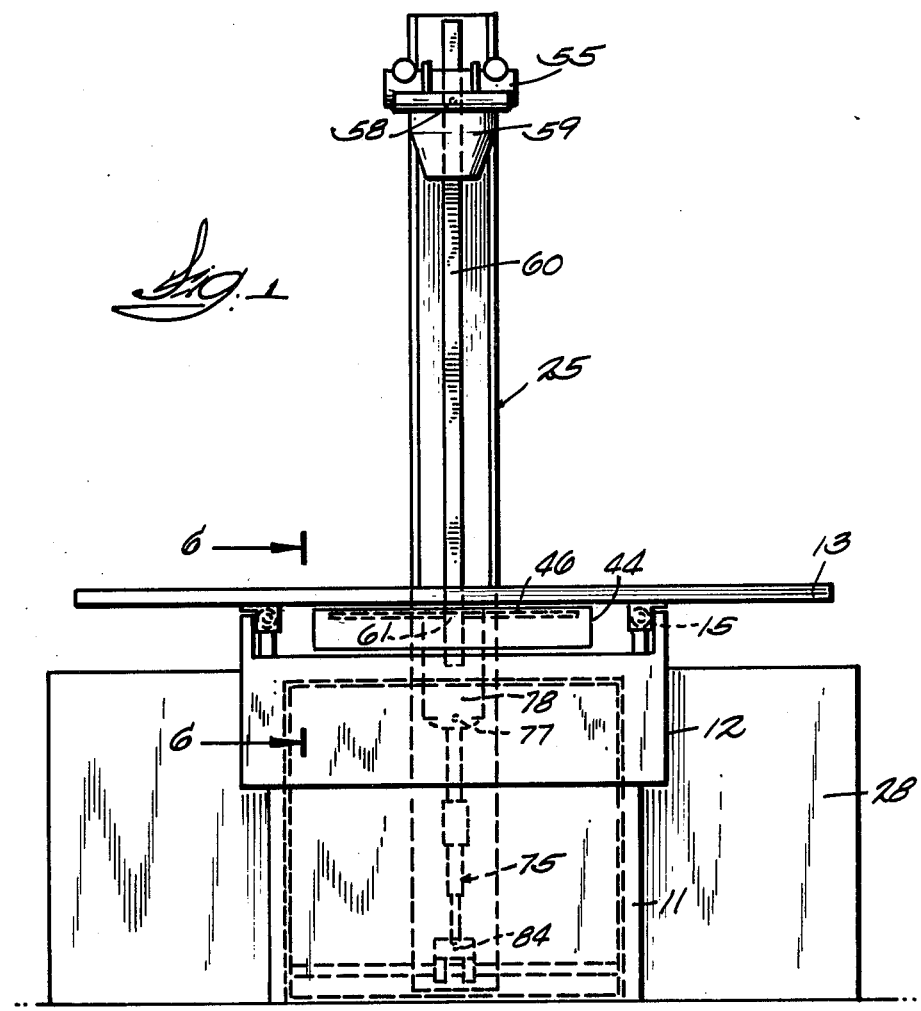
Fig. 1
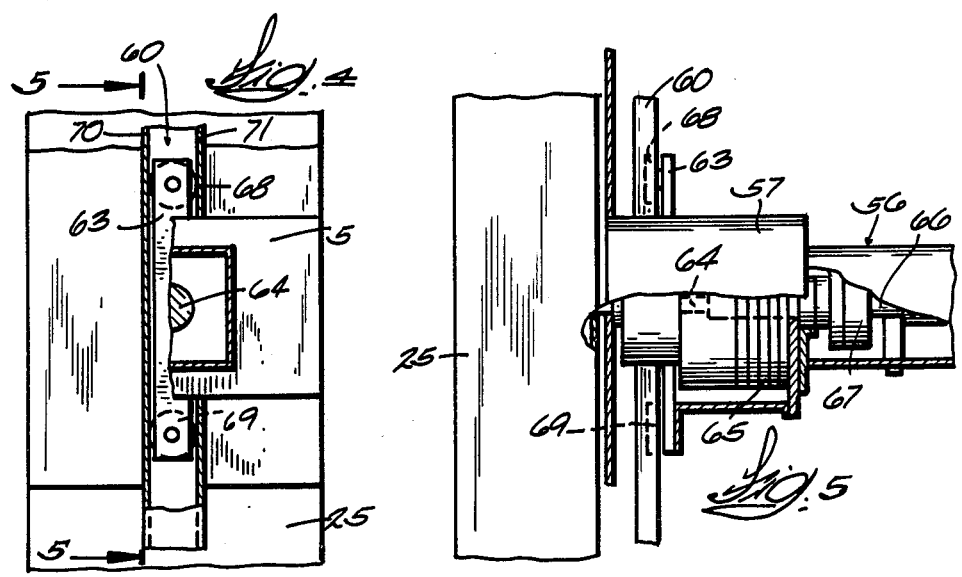
Fig. 4
Fig. 5

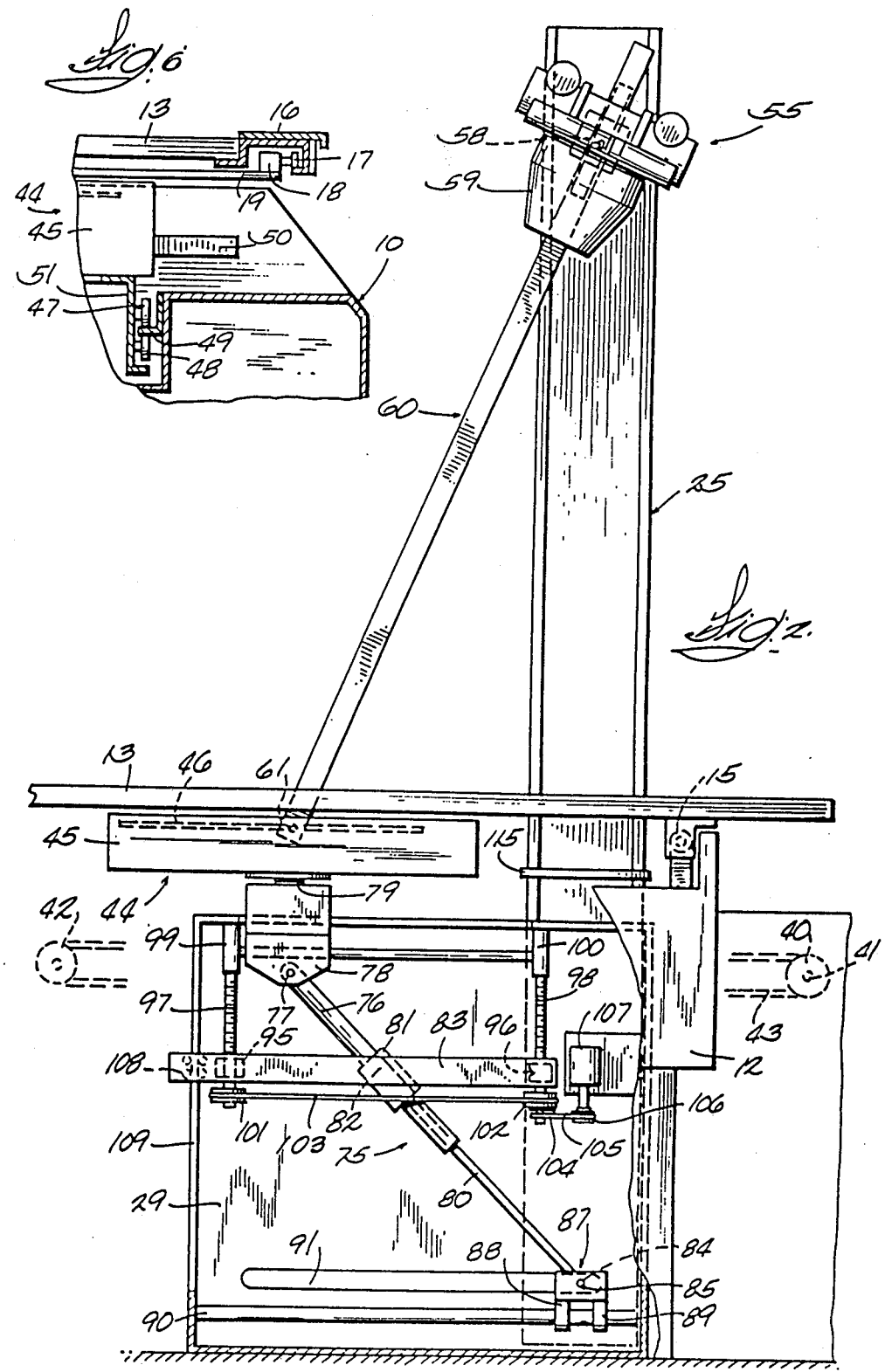

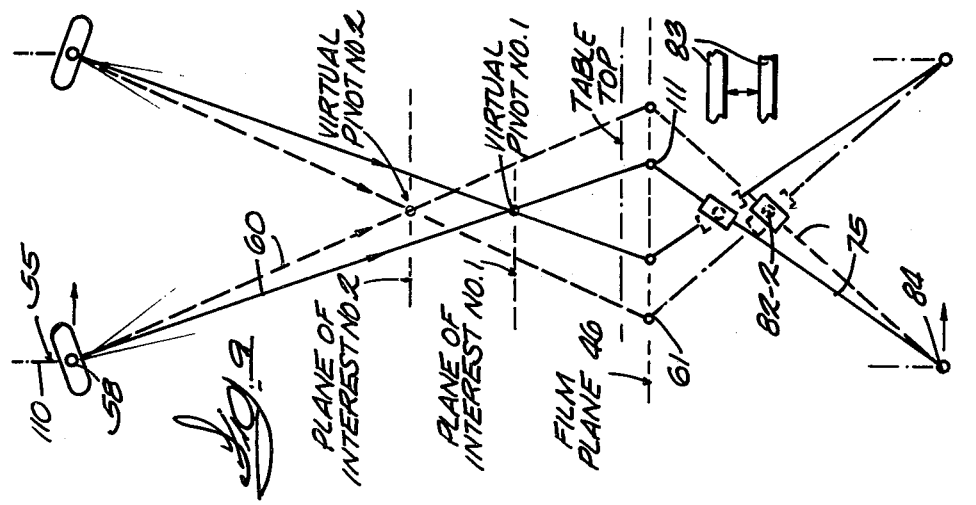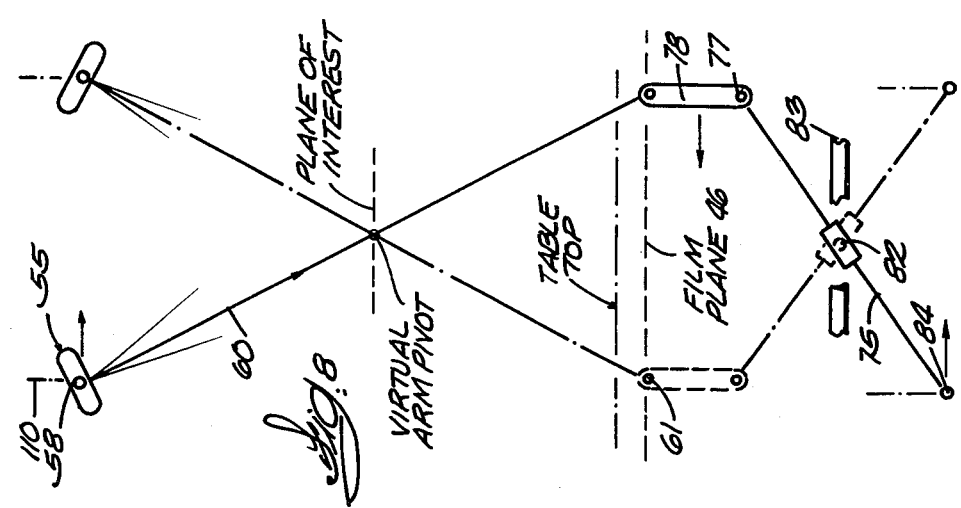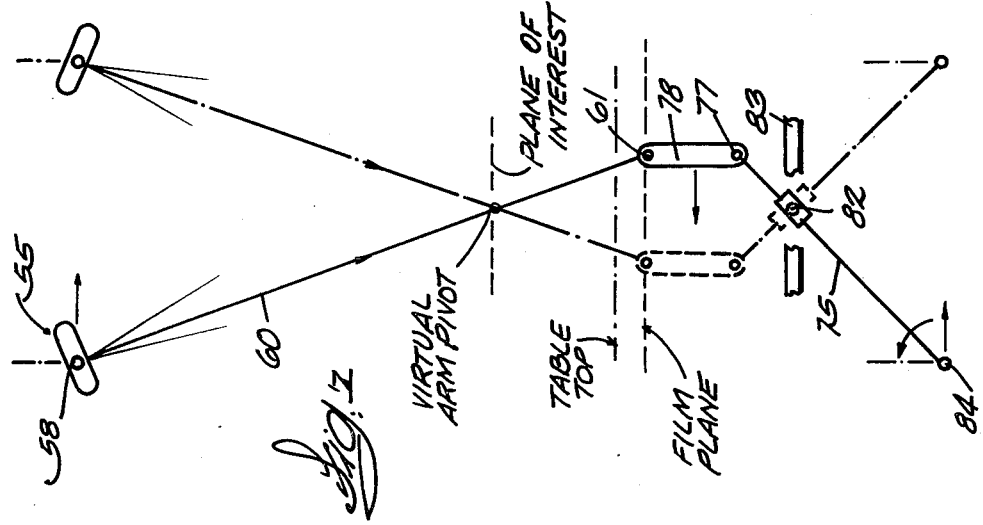

X-RAY TOMOGRAPHY TABLE HAVING A VIRTUAL FULCRUM ARM PIVOT

BACKGROUND OF THE INVENTION

This invention relates generally to diagnostic x-ray apparatus and particularly to an x-ray table system that is adapted for performing conventional radiography and tomography.

For conventional radiography, the patient is positioned on an x-ray transmissive table top. An x-ray tube is stationarily located above the patient and an x-ray image receptor, such as a film in a bucky tray, is stationarily located below the patient in the table housing. The focal spot of the x-ray tube is usually located over the center of the film and the central ray of the x-ray beam is usually perpendicular to the film plane. The differentially attenuated x-ray image that results from the x-ray beam penetrating the patient is projected onto the film in a cassette within the bucky tray so the image is recorded on the film. In projection radiography various organs including tissue and bone that are actually at different levels in the body are superimposed on the projected image on the radiographic film and give the appearance of lying in a single plane or level within the body. Sometimes this makes interpretation of the radiograph difficult.

As is known, projection tomography permits recording on film and visualization of a relatively thin single plane or level in the body by blurring or making uniformly gray all layers in the anatomy above and below the plane of interest. For performing tomography, the patient is positioned on the x-ray table top and the x-ray source is energized and translated in one direction along a horizontal line at a fixed distance from the plane of interest in the patient while the bucky tray containing the film cassette is translated in the opposite direction at a fixed distance from the plane of interest. As the x-ray tube is translated it is also rotated so that the central ray remains directed through the same point, usually the center, of the radiographic film. Coordinate opposite movement of the x-ray tube and bucky is usually achieved by connecting the bucky and x-ray tube together with a telescoping fulcrum arm. This arm is parallel to the central ray of the x-ray beam. A bracket or carriage is typically fixed at a side of the x-ray table top and extends above the top. The bracket has an element that can be raised or lowered relative to the plane of the table top. The fulcrum arm pivots on this element. The pivot axis is coincident with the plane of interest in the patient. Because the pivot axis is on the plane of interest, there is no relative movement between this plane and the x-ray beam, whereas, there is relative movement of the planes above and below the plane of interest so said planes are blurred in the projected image and a relatively sharp image of the plane of interest remains.

The traditional bracket that extends above the x-ray table top and provides the adjustable pivot element constitutes an interference with some x-ray procedures that are intended to be performed with x-ray apparatus of the type hereunder consideration. For example, the x-ray tube is usually mounted on a vertically extending column that is driven translationally in order to translate the x-ray tube and bucky as is required for tomography and as is required for ordinary radiography where the x-ray tube focal spot and central ray must be kept in alignment and perpendicular to the film plane. For some procedures, however, it is necessary to rotate the x-ray tube for projecting its beam, particularly its central ray, parallel to the table top instead of perpendicularly or at a limited angle away from perpendicular as is required for radiography. For example, for some procedures the patient is not located on the x-ray table top but is standing at some distance from the table in juxtaposition to a wall-mounted film cassette that can be raised and lowered to align with the anatomy of interest in the patient. At the same time, the x-ray tube must be rotated to cause its central ray to be projected horizontally and must be raised or lowered to align with the anatomy of interest so the projected image will fall on the film cassette. Very often, the tomographic arm bracket or pivot element support interferes with the beam path, especially when it is desired to radiograph the lower part of a patient who is standing in juxtaposition to a wall-mounted film cassette. Interferences can also occur when an attempt is made to project the x-ray beam laterally of the table top through a patient lying thereon for imaging on a film that is held in a vertical plane.

U.S. Pat. Nos. 3,838,286 and 4,335,312 illustrate tomographic apparatus wherein the tomographic fulcrum arm adjustable level pivot element is located in a structure that extends above the x-ray table top. U.S. Pat. No. 4,315,156 illustrates an x-ray table adapted for tomography wherein having the fulcrum arm pivot located above the table top is avoided by using a complicated mechanism wherein elements corresponding to the tomographic fulcrum arm and its pivot are located below the table and the action that they produce is transmitted through a shaft which angulates the x-ray tube during tomography and is concealed within the column that supports the x-ray tube for angulation and translation.

SUMMARY OF THE INVENTION

The invention resides in providing an x-ray table that has a new mechanism for operating the system in a tomographic imaging mode wherein there is no actual fulcrum pivot and bracket therefor extending above the table top but, instead, there is an imaginary or virtual pivot for the tomographic fulcrum arm that extends between the x-ray tube and an image receptor plane such as a radiographic film plane within a bucky carriage.

In accordance with the invention, the x-ray table that incorporates the invention has some conventional parts comprising a base, an x-ray transmissive table top over the base, an upright column mounted for moving longitudinally of the table top, means for moving the column, carriage means for an image receptor such as a film cassette under the table top for moving longitudinally thereof, an x-ray tube and means supporting the tube on the column above the table top for selectively moving toward and away from the table top and for selectively angulating about an axis that extends laterally of the table top and is substantially perpendicular to the plane of the column movement.

The new means for adapting the general purpose x-ray table system for performing tomography comprises a vertically movable support member under the table top and guide means mounted on the support member for rotating about a laterally extending rotational axis. An extensible and contractible (telescoping) link means mounted in the guide means for rotation therewith with one end of the link means pivotally connected above the rotational axis to the receptor carriage means and the other connected below the rotational axis to the movable column. An extensible and contractible (telescoping) arm means connected at one end to the receptor carriage for pivoting about an axis coincident with the image receptor plane and connected at its other end to the x-ray tube support for angulating the x-ray tube in a manner that maintains its central ray in parallelism with the arm means and directed to substantially the same point on the image receptor plane during a tomographic procedure. Movement of the column in one direction causes the link means that is below the table top to pivot and move the image receptor carriage in the opposite direction and causes the arm that is above to swing about a laterally extending virtual axis coincident with a plane of interest in a body positioned on the table top. The set distance of the link pivot axis from the image plane determines the distance from the image plane to the virtual arm pivot axis which lies on the plane of interest.

A more detailed description of the new mechanism for adapting an x-ray table to perform tomography will now be set forth in reference to the drawings.

DESCRIPTION OF THE DRAWINGS

FIG. 1 is a front elevation view of an x-ray table system in which the new tomographic mechanism is incorporated;

FIG. 2 is a front elevation of the x-ray table with parts being broken away to expose the tomographic linkage and with the upright column, that appears centered with the x-ray table top in FIG. 1, shifted toward one end of the table where it resides at the end or beginning of a tomographic procedure;

FIG. 4 is a vertical section taken on a line corresponding with 4—4 in FIG. 3;

FIG. 5 is a partial vertical section taken on a line corresponding with 5—5 in FIG. 4;

FIG. 6 is a partial vertical section taken on a line corresponding with 6—6 in FIG. 5;

FIGS. 7, 8 and 9 are diagrams that are useful for explaining the principles of the new tomographic drive system.

DESCRIPTION OF A PREFERRED EMBODIMENT

Figure 3:
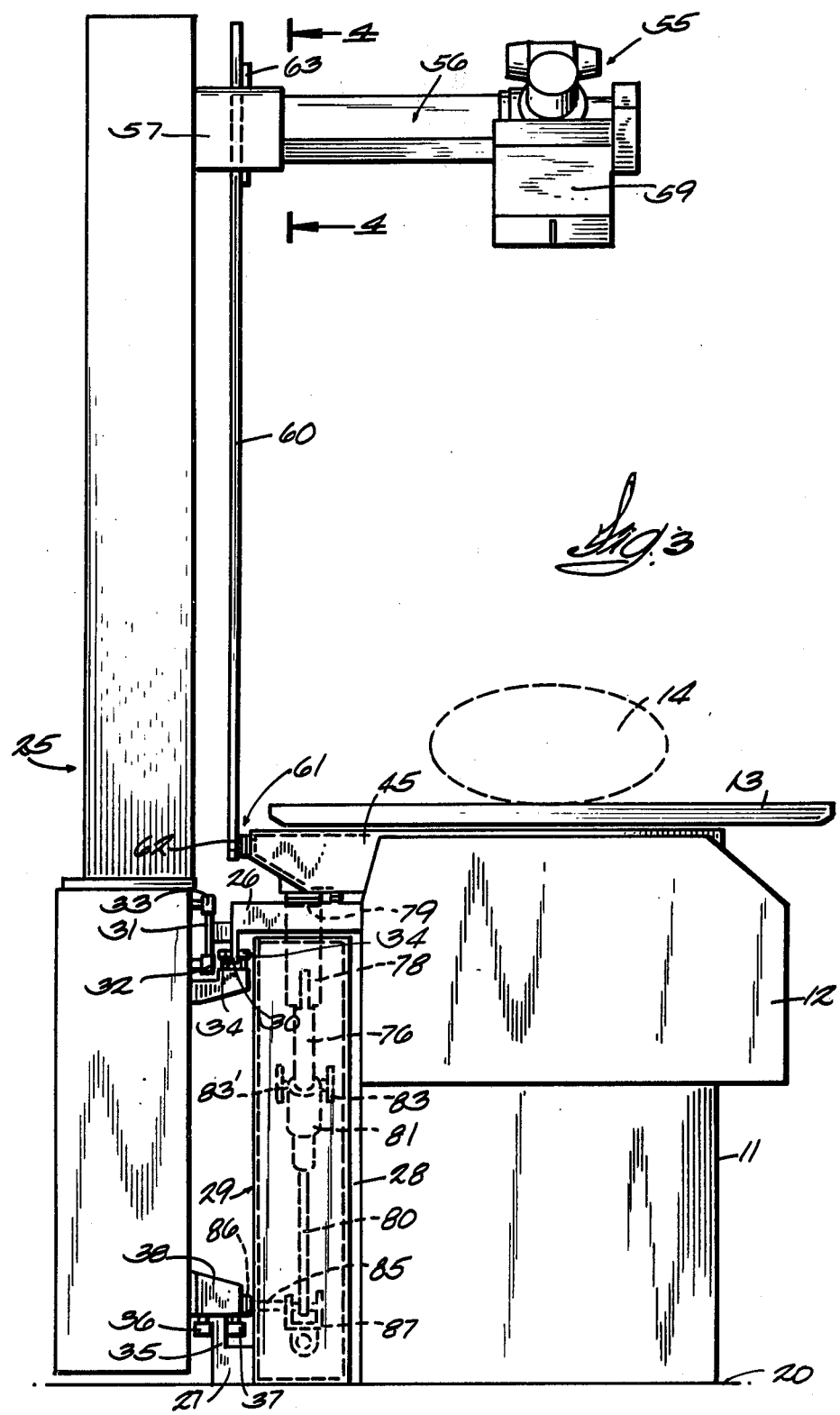
FIG. 3 is a left end elevational view of the x-ray table depicted in the preceding figures.

Referring to FIGS. 1–3, the x-ray table comprises a base or housing that is generally designated by the reference numeral 10. Base 10 is comprised of a metal box 11 to which is affixed an upper overhanging box 12 that has an opening in its top. An x-ray transmissive table top 13 is arranged over the top opening in box 12. The ellipse marked 14 in FIG. 3 symbolizes the body of a patient who is lying on a table top 13 and who could be ready for an ordinary projection radiography procedure or a tomographic procedure. Table top 13 is mounted for moving relative to base 10 longitudinally, that is, to the left or right as viewed in FIGS. 1 and 2 and is also movable laterally, that is, toward and away from the observer as in FIGS. 1 and 2 and to the left or right as viewed in FIG. 3. For the sake of establishing uniform terminology, the lateral direction is the direction across the narrow dimension of the table and the longitudinal direction is the direction along the length of the table top.

As can be seen in FIG. 1, the table top 13 is moved laterally relative to base 12 on linear bearings such as the one marked 15 which slide on rods that are fixed to the table top. As shown in FIG. 6, table top 13 is provided with a parallel pair of longitudinally extending rails 16 that ride on rollers 17 whose axes extend laterally. The shafts for the rollers extend from blocks such as the one marked 18 and these are mounted on the edges of a plate 19 which, although not visible, has a large opening in it to allow an x-ray beam to pass through from above into the upper part of base box 12.

An upright or vertical column, generally designated by the numeral 25, is mounted for moving longitudinally of the table top 13 in an upright attitude as is shown in the illustrative x-ray table. Column 25 is supported from a frame or fixed base comprised of upper and lower laterally extending and longitudinally extensive track members 26 and 27, a back plate 28 and a box-like housing 29. Members 26–29 can be considered to be part of the x-ray table base. These members could be free standing on floor 20 and separated from the remainder of base 10. Upper member 26 has longitudinally extending tracks or rails 30 and 31 fastened to it. As shown in FIG. 3, rollers such as those marked 32 and 33 are journaled for rotation on column 25 and provide some support for the column on rail 31. Another set of rollers such as the one marked 34 are also journaled for rotation on column 25 to prevent the column from tilting toward or away from base 10 and yet let the column move longitudinally along rail 30. The lower member 27 is also provided with a longitudinally extending rail 35 which fits between pairs of rollers 36 and 37 that are journaled on a bracket 38 which is fastened to column 25. Thus, the rollers and rails just described permit column 25 to be driven longitudinally and in parallelism with the x-ray table top 13. There is clearance between the bottom of column 25 and the floor line 20 so the column is suspended above the floor in this embodiment.

Drive mechanism for column 25 is shown only schematically in FIG. 2 where it is seen to comprise a fixedly mounted reversible electric motor 40 having a sprocket 41 on its shaft. Spaced from sprocket 41 in the x-ray table housing is an idler sprocket 42. A chain 43 runs on each of the sprockets. Although it is not visible, the top run of chain 43 is connected to column 25 so that when reversible motor 40 turns as is the case during a tomographic procedure, column 25 will move in one longitudinal direction or the other depending upon the rotational direction of the motor.

Referring to FIG. 2, an x-ray image receptor device is mounted under table top 13 for moving longitudinally thereof. The device is generally designated by the reference numeral 44 and, in this case, is a bucky carriage. The bucky carriage is basically a box 45 as shown in FIG. 3 where the tracks for constraining it or to move longitudinally of the x-ray transmissive table top 13 have been omitted for the sake of clarity. The actual receptor or x-ray image recording medium in this example is a radiographic film 46 which is shown in dashed lines in FIG. 2 within the bucky carriage. The tracks on which the image receptor or bucky carriage 45 translates can be seen in FIG. 6. This figure shows bucky carriage 45 has an inverted U-shaped base providing parallel longitudinally and vertically extending sides such as the one marked 51 on which upper and lower rollers 47 and 48 are journaled. The rollers run on a longitudinally extending track 49 which is mounted to base housing 10. A handle 50 is shown extending from the bucky in FIG. 6. This handle is attached to a tray, not shown, that holds a film cassette, not shown, in which the recording medium or radiographic film 46 is retained.

As shown in FIG. 3, an x-ray tube casing 55 is mounted to translatable column 25 through the agency of an arm 56 which extends into a mechanism housing 57. Although the details are not shown, laterally extending arm 56 is mounted in column 25 for vertically adjustable movement on column 25 and the arm can be locked at any desired level relative to the imaging plane, that is, to the plane of radiographic film 46 in the bucky carriage which vertical locking is required when the apparatus is being operated in the tomographic mode wherein the x-ray tube 55 moves longitudinally at a constant height above table top 13. As will be explained, however, arm 56 and, hence, the x-ray tube, not shown, in casing 55 are allowed to angulate about a laterally extending axis while translating longitudinally during a tomographic cycle. The x-ray tube casing 55 is shown in one of its angulated positions in FIG. 2 in which it may be at the beginning or end of a tomographic procedure cycle.

Referring to FIG. 2, the laterally extending angulation or rotation axis for the x-ray tube casing is marked 58. The focal spot of the x-ray tube that is in casing 55 lies on axis 58. An x-ray beam collimator 59 is coupled to x-ray tube casing 55. The collimator is conventional and is used for defining the boundaries of the x-ray beam that emanates from the focal spot of the x-ray tube. A tomographic fulcrum arm 60 forms a connection between a point coinciding with the rotational or angulation axis 58 of the x-ray tube and the plane of the film 46 in the bucky carriage. As can be seen in FIG. 3, the lower end of fulcrum arm 60 makes a pivotal connection to the rear end of bucky carriage 45 at a place to which the arrowhead on the lead line from the reference numeral 61 points. The numeral 61 is used to designate the pivot axis of said connection between fulcrum arm 60 and the bucky carriage 45. A device 62 is also provided for enabling the lower end of arm 60 to be coupled to bucky carriage 45 as is required for conducting tomography and to be uncoupled as may be required for performing other x-ray procedures. For some of said other procedures, wherein fulcrum arm 60 is uncoupled from the bucky carriage at the pivot axis 60, said arm is clamped to column 25 by means which are not shown so the arm will not swing freely.

Since for performing tomography, the x-ray tube focal spot must be moved at a constant vertical distance from the imaging plane of the film and an extrapolation thereof, and since fulcrum arm 60 angulates in a vertical plane for following the bucky carriage 45 which moves in one direction while the vertical column 25 moves in the opposite direction it is necessary to compensate for the change in the length of the arm resulting from such movements of the column and x-ray tube and the bucky. Hence, fulcrum arm 60 is allowed to telescope or slide relative to the lateral axis on which the x-ray tube focal spot resides. As can be seen in FIGS. 4 and 5, this is accomplished by using a guide bar 63 which is attached at its center to a laterally extending shaft 64. A clutch device has the capability of coupling shaft 64 to another coaxial shaft 66 on whose axis the x-ray tube angulates during tomography. An electromagnetic operator 67 is operative to engage and disengage clutch 65. As stated, the clutch is engaged and the two shafts 64 and 66 are coupled for tomography. Guide bar 63 is provided with upper and lower rollers 68 and 69 which ride between the edge flanges 70 and 71 of channel shaped fulcrum arm 60 as can be seen clearly in FIG. 4. In any event, it will be evident that fulcrum arm 60 can move transversely to the axis of shaft 64 to thereby execute a sliding action to compensate for the changing x-ray tube focal spot-to-film distance as the x-ray tube and bucky are translated oppositely during tomography. As an alternative fulcrum arm 60 could be formed with aligned telescoping sections, not shown, and the lower end of one section could be pivotally connected to the bucky carriage at axis 60 and the upper end of the other end could be connected for pivoting on the coincident axis of shaft 64 and tube rotational axis 58. Any arm that pivots, compensates for the distance changes between the x-ray tube and film during tomography and keeps the central x-ray aligned with the center of the film could be used.

The x-ray table structure thus far described is basically conventional except for the feature of having the tomographic fulcrum arm 60 pivotally connected directly to the bucky image receptor on an axis 61 that lies on the image plane in the receptor 44 and, more specifically, on the plane of film 46 in the illustrated embodiment. Most commonly, in prior art x-ray tables that are adapted for tomography on the other hand, the lower end of the fulcrum arm is pivotally connected to the bucky carriage and a point above this end is pivoted to a bracket that extends above the x-ray table top and the elevation of this pivot is adjusted to determine the coincident plane at which a tomographic layer will be imaged. The new mechanism for causing the tomographic fulcrum arm 60 to pivot about a virtual or imaginary pivot axis at a predetermined height above the table top and coincident with the layer in the body that is to be imaged without using a bracket or other means to support the pivot will now be described in greater detail.

Referring to FIG. 2, as has been explained, bucky carriage 45 is mounted under table top 13 for moving in either longitudinal direction, to the right and back to the left for executing a tomographic cycle. As viewed in FIG. 2, the bucky carriage is moved under the influence of an extensible and contractible or telescopic link means that is generally designated by the reference number 75. In this embodiment, the link means 75 comprises a tubular link member 76 that is pivotally connected at 77 to a bracket 78 which is coupled to bucky carriage 44. The coupling is shown schematically and is indicated by the numeral 79. This coupling 79 can be an electromagentic lock or a mechanical type lock which is activated or engaged to couple the bucky carriage to bracket 78 at least when tomography is to be performed. Link means 75 further comprises a rod 80 or shaft which extends into and is slidable in tubular link member 76. Tubular member 76 is slidable in a sleeve element or guide means 81. Element 81 is pivotally attached for rotation about a laterally extending axis 82 on a vertically adjustable support member 83. The lower end of link member 80 and, hence, link means 75 is connected to longitudinally translatable column 25 for the link means to pivot at its lower end about a laterally extending axis indicated by the reference numeral 84 in FIG. 2. How this pivotal connection is made is more evident in the lower left region of FIG. 3. Here one may see that there is a shaft or pin 85 whose axis is identified by the numeral 84 in FIG. 2. There is another coupling and decoupling device 86 interposed between pin 85 and the bracket 38 by which the pin is effectively connected to the lower end of longitudinally translatable column 25.

Referring to FIG. 2 again, observe that when the mechanism is set up for tomography, pivot axis 84 at which the lower telescoping link means 75 connects to column 25 is in direct vertical alignment with the upper pivot axis 58 for the x-ray focal spot which is equivalent to the pivot axis for fulcrum arm 60. In other words, for tomography, the axis 58 about which x-ray tube angulates relative to column 25 is always vertically aligned with axis 84 about which the lower end of link means 75 swings relative to the column 25 since axes 58 and 84 move together with column 25.

The pin 85 by which the lower end of link means 75 member 80 is connected to the movable column 25 is fixed in a guide clevis member that is numbered 87 in FIGS. 2 and 3. Member 87 has two circular extensions 88 and 89 in which there are linear bearings. These bearings guide member 87 rectilinearly along a stationary rod 90. Thus, for example, when the column 25 is driven to the left from where it is in FIG. 2 the lower link means axis 84 will be translated to the left along a straight horizontal line under the guidance of the linear bearings running on rod 90. When link means pivot 84 is driven to the left, bucky carriage 45 is driven in parallelism to the right and vice versa. When such column driving occurs, link means 75 telescopes or shortens until it attains a vertical attitude after which it begins to extend again. Such extension ends when longitudinal movement of column 25 terminates. It should be noted in FIG. 2 that there is a slot 91 in the back plate 29 through which pivot pin 85 and its axis 84 projects.

The elevation of the pivot axis 82 for the extensible and contractible link means 75 below the table top is adjustable. The sleeve element or guide means 81 in which link member 76 slides is pivotally connected between a pair of parallel support bars one of which, 83, is visible in FIG. 2 and the other of which, 83', is also visible in FIG. 3. As shown in hidden or dashed lines in FIG. 2, there are a pair of internally threaded follower nuts fastened between support bars 83 and 83' and marked 95 and 96. Lead screws 97 and 98 are threaded into these nuts. The upper end of lead screw 97 is journaled for free rotation in a bearing bracket 99 and the upper end of lead screw 98 is journaled for rotation in a bracket 100. Joint rotation of lead screws 97 and 98 in one direction will, as a result of the lead screws extending through follower nuts 95 and 96, elevate the link pivot support means 83, 83' and the sleeve 81 of pivot axis 82. Rotation of the lead screws in the opposite direction will, of course, lower the support means 83 and link pivot sleeve and axis 82 also. The lead screws 97 and 98 have toothed pulleys 101 and 102 fastened to them. The pulleys have a closed loop toothed belt 103 running on them for turning the lead screws in synchronism. Lead screw 98 has another pulley 104 fastened to it and this pulley is connected by means of a belt 105 to a pulley 106 on the shaft of a reversible motor 107. Thus, when the motor 107 turns in one direction, support means 83, 83' is raised and when the motor turns in the opposite direction the support means is lowered. In an actual embodiment, the motor is energized at the command of the user who adjusts the elevation of telescopic link means 75 pivot axis 82 in accordance with the plane of the body lying on the table top that is to be imaged. In an actual embodiment, means, not shown, are provided for indicating to the operator the height of the plane above the table top where the virtual pivot for the tomographic fulcrum arm 60 exists and this corresponds to the height of the plane that is to be imaged and is proportional to the distance between the lower link pivot 82 and the film plane 46 in the bucky carriage 46.

Support means 83 for the link pivot means is further guided vertically by a set of rollers 108 that run along the edge of a side member 109. This contributes to maintaining the support means 83, 83' level and undistorted when the lead screws 97 and 98 are being driven rotationally.

Now that the parts of the apparatus that are pertinent to performing tomography have been described, the geometrical relationship of the parts for obtaining a virtual pivot axis for fulcrum arm 60 and for establishing the height above the film plane of the layer in the body that will be imaged on the film will be considered.

Refer to the FIG. 9 diagram which shows the link 75 pivot axis 82 at two different levels of adjustment for radiographing correspondingly different layers of interest in a body lying on x-ray transmissive table top 13 above the film plane 46. The geometry in FIG. 9 is equivalent to the actual embodiment which is diagrammed in FIGS. 7 and 8 as will be discussed in more detail later. In FIG. 9, for one set of conditions the location of the pivot axis for the telescoping link means 75 is designated by the reference numeral 82-1. The telescopic link means 75 is shown in solid lines as is the tomographic arm 60 which is actually in parallelism with the central ray of the x-ray beam which is designated by the same number. In this example of the geometrical principles the upper end of telescoping link means 75 is pivotally connected at an axis 61 that is coincident with film plane 46 in the bucky carriage as opposed to it being connected to a bracket at axis 77 below the film plane as depicted in the realistic FIG. 2 embodiment. In FIG. 9, the fulcrum arm 60 is also connected to the bucky carriage on axis 61. In FIG. 9 the lower end of telescopic link means 75 is fastened at pivot axis 84 to the lower end of the column 25 and the axis of rotation 58 for the x-ray tube 55 is on the same vertical line 110 as is the lower link means pivot axis 84.

Assume that production of a tomographic image is about to start using the FIG. 9 geometry and that the x-ray tube 55 and its focal spot and its lateral axis 58 and the lower link pivot axis 84 are in their leftmost position in the region where the reference numeral 111 is applied. Now for tomography the upright column 25 is driven to the right in FIG. 9 and the focal spot axis 58 of the energized x-ray tube and the lower link means pivot axis 84 are being carried to the right horizontally at a fixed elevation with respect to film plane 46. The central ray of the x-ray beam, being in parallelism with fulcrum arm 60, is directed to the point or line on the film that is coincident with pivot axis 61 at which the upper fulcrum arm 60 and lower link means 75 are pivotally connected to the bucky carriage in this case. The fulcrum arm 60 and link means 75 are shown in solid lines. The central x-ray and fulcrum arm axis 60 are directed through a virtual pivot which is indicated as virtual pivot No. 1 in FIG. 9. This ray continues to pass through the virtual pivot No. 1 at the same height above the film plane and finally the x-ray tube 55 reaches its rightmost position as viewed in FIG. 9. Since the distance between the link pivot axis 82-1 is adjusted to a fixed distance from film plane 46, virtual pivot No. 1 must necessarily remain at a constant distance above film plane 46. Of course, the tomographic arm 60 compensates for distance changes between the x-ray tube and the film plane as the x-ray tube translates by the relative sliding action between the arm 60 and the x-ray tube but the level of the virtual pivot and, hence, the plane of interest in the body on the table top remains constant.

FIG. 9 shows what happens when the pivot 82 for link means 75 is lowered to the position wherein the pivot is designated 82-2. Arm 60 and link means 77 are depicted in dashed lines in this example. The beginning and end positions of the slidable distance compensating fulcrum arm 60 and central ray are shown in dashed lines as is the telescoping linkage 75 in this example. One may see that link means pivot 82-2 is at the depicted elevation, the virtual pivot for fulcrum arm 60 is higher than in the previous case and is designated as virtual pivot No. 2 which again lies on and defines the plane of interest No. 2. Thus, it can be seen that lowering link pivot axis 82 raises the virtual pivot axis of the arm 60 and raising link pivot axis 82 lowers the virtual pivot axis of the arm.

The geometrical relationships in the FIG. 9 diagram are accurate but the dimensions of the arms and links are out of proportion to obtain better emphasis and clarification of what happens when the lower link means pivot is established at different elevations.

FIG. 7 is a geometrical diagram that corresponds more closely to the structure that has been described. In this case the telescoping link means 75 has its lower end connected at pivot axis 84 for pivoting on column 25 and has its upper end pivot axis connection at 77 which is on bracket 78 that extends downwardly from the bucky carriage 45. The pivot axis 82 in FIG. 7 has been adjusted to the indicated height. When the column 25 and concomitantly upper fulcrum arm 60 pivot 58 and lower link means pivot 84 are moved together to the right in FIG. 7 the central ray of the x-ray beam and the plane of the fulcrum arm 60 pass through the virtual arm pivot point which is identified by that legend in FIG. 7 and is on the plane of interest as indicated. At all times that the x-ray tube 55 is moving toward its final or rightmost position in FIG. 7, the central ray of the x-ray beam which parallels the fulcrum arm is directed through the virtual arm pivot axis as before. Thus, if for practical reasons such as avoiding interference of moving components, the link means 75 pivot can be connected at axis 77 even through this axis is at some distance below the film plane 46. In any case, the vertical distance between the adjustable height link means axis 82 and its point of connection 77 to the bucky carriage determines the distance between the plane of interest in the body and the film plane.

The FIG. 8 diagram is comparable to FIG. 7 except that in FIG. 8 lower link means pivot 82 has been adjusted downwardly compared to FIG. 7. Thus, in the FIG. 8 diagram, the virtual arm pivot which coincides with the plane of interest in the body is at a greater distance from the film plane than in the case of FIG. 7.

As is known in tomography, there is no motion occurring at the fulcrum axis level because the image projection from the fulcrum arm pivot level falls at exactly the same point on the radiographic film at all times during the joint motion of the x-ray tube and film. Blurring due to motion does not result in the fulcrum plane. Any plane above or below the fulcrum pivot axis level has its projections displaced from one end of the film to the other during a bucky carriage excursion. As can be seen from the FIG. 7-9 diagrams, any point at the right edge of the film at the start of an excursion ends at the left edge of the film at the end of the excursion. This causes blurring of the areas above and below the fulcrum axis be it real as in the prior art or virtual or imaginary in accordance with the invention.

It is evident that there will be less blurring of layers above and below the fulcrum level if the layers are closer to the fulcrum level since the amount of motion and displacement would then be reduced. Any planes farther from the fulcrum level in the body would increase the amount of motion and displacement and increase the degree of blurring on the film.

A thin body section shows better detail in the radiograph than a thick one. Two factors control establishing the thickness of a section that will be imaged on the film. One factor is the amplitude or the amount of x-ray tube horizontal travel. A short amplitude will produce a thick section because the motion above and below the fulcrum point is at a minimum and little blurring occurs. An increased amplitude results in a thinner section because of the increase in the motion above and below the fulcrum axis level causing blurring closer to this level.

The other factor involved in controlling thickness of a body layer is the x-ray tube focal spot-to-film distance. For any given x-ray tube amplitude, the shorter the distance the thinner the section will be because there is a greater area of motion and more blurring takes place in the planes above and below the fulcrum axis level. Conversely, the greater the focal spot-to-film distance, the thicker the section will be.

The fact that the x-ray tube can be established at a fixed height on column 25 in preparation for tomography has been discussed previously and provides for establishing any desired and practical focal spot-to-film distance. Predetermining the x-ray tube travel or amplitude during tomography can be obtained by turning the x-ray tube on and off automatically when the x-ray tube is at exposure start and exposure stop positions, respectively. The means for doing this are not shown because they are known to those skilled in the art.

Only so much of the x-ray apparatus has been shown and described as is required to bring out the manner in which the new virtual pivot tomographic mechanism is constructed and operated. The actual x-ray table apparatus is, of course, capable of producing ordinary direct projection radiographs wherein the x-ray beam is either projected vertically through the body or angularly by rotating the x-ray tube and shifting the tube or focal spot through the point where the central ray of the x-ray beam is at the desired angle relative to the anatomy of interest.

Considering FIG. 1, the apparatus is designed so that when the column 25 is in the center of the table as depicted, actuation of the coupling lock 61 will lock the fulcrum arm 60 against rotation on the bucky carriage so it will move in line with the x-ray beam when column 25 is shifted. At the same time, lock 86 may be engaged to prevent rotation of tomographic link means 75 and maintain the link means in alignment with or parallelism with fulcrum arm 60. For ordinary vertical radiography x-ray tube 55 may also be locked against rotation. With these conditions prevailing, the central ray of the x-ray beam will be directed perpendicularly to the film plane and through the center point of the film regardless of the longitudinal position of the column 25.

If it is desired to make an ordinary projection radiograph with the x-ray beam at an angle relative to the body instead of being vertical as just discussed, lock 86 is uncoupled so the link means 75 is allowed to swing without resistive force and the lock 61 is uncoupled but still allows the lower end of the fulcrum bar to pivot relative to the bucky so that the fulcrum arm can achieve various angles relative to the table top for angular radiography. In such case, the x-ray tube is unclutched so it can rotate about its axis which is coincident with the focal spot and the central ray of the x-ray beam will remain parallel to the fulcrum arm 60 when the x-ray tube is rotated due to moving column 25 longitudinally. In this case, the bucky carriage is also locked and the patient on the table top is put in the proper position for radiographing the region of interest by moving the table top 13 laterally or longitudinally, as required.

In the actual apparatus, column 25 is constructed for allowing rotation about a vertical axis. Referring to FIG. 2, column 25 may be divided into upper and lower parts which are rotatable about a plane indicated by the numeral 115 in FIG. 2 a short distance below table top 13. The column 25 may be rotated when it is desired to get the x-ray tube displaced from the column in one longitudinal direction or the other so that a lateral radiographic view of a patient lying on the table top may be made using a film cassette which is detachably mounted to the table top and has its film or image plane disposed vertically. For procedures which require rotation of column 25 about a vertical axis, fulcrum arm 60 must be uncoupled from the bucky carriage and clamped to column 25 by means which are not shown.

Although apparatus for obtaining a virtual fulcrum arm pivot by using adjustable mechanical means to establish the pivot point has been described in considerable detail, such description is intended to be illustrative rather than limiting, for the inventive concepts may be variously implemented so the scope of the invention is to be determined only by interpreting the claims which follow.

I claim:

1. Diagnostic x-ray table apparatus comprising means for performing tomography and other x-ray procedures and having a base, an x-ray transmissive table top supported from the base, a column extending above and below the table top and mounted for moving longitudinally of the table top, means for moving the column, carriage means for an image receptor having an imaging plane, said carriage means mounted below the table top for moving longitudinally of said top, x-ray tube means and means supporting said tube means from said column above said table top for said tube means to angulate about an axis that extends laterally of the table top and is substantially perpendicular to the plane of column movement, said means for performing tomography including:

support means under the table top and means for securing said support means at a predetermined distance from said imaging plane, extensible and contractible link means and means for pivotally connecting said link means intermediate of its ends to said support means for enabling said link means to swing about a laterally extending pivot axis, one end of said link means being pivotally connected to one side of said pivot axis to said receptor carriage means and the other end being pivotally connected on the other side of said pivot axis to said movable column, fulcrum arm means pivotally connected at one end to said image receptor carriage means for pivoting about a laterally extending axis coincident with said image receptor imaging plane and coupled at its other end to said x-ray tube supporting means for angulating with said x-ray tube supporting means during longitudinal movement of said column in a manner that maintains the central ray of the beam from the x-ray tube in substantial parallelism with the fulcrum arm means and directs said ray to substantially the same point on said image receptor plane during a tomographic procedure, movement of said column in one direction causing said link means to swing on its support means and move said image receptor carriage in the opposite direction and causing said arm means to swing about a laterally extending virtual axis coincident with a plane of interest in a body positioned on said table top which plane of interest is at a distance from said image plane determined by the distance at which said link means pivot axis is set relative to said image plane such that an x-ray beam projected by said x-ray tube through said body will produce a tomographic image of said plane of interest on said receptor image plane.

2. The apparatus as in claim 1 including:

means for moving said support means and, hence, the pivot axis for said link means to obtain various of said predetermined distances from said pivot axis to said imaging plane, whereby when said pivot axis is moved away from said imaging plane along a line perpendicular to said plane the distance between said virtual axis and said imaging plane will increase proportionally and when said axis is moved toward said imaging plane said distance between said virtual axis and said imaging plane will decrease proportionally.

3. The apparatus as in claim 2 wherein said means for moving said support means comprises:

internally threaded means fastened to the support means, lead screw means threaded into said internally threaded means and means journalling the lead screw means for rotation, reversible motor means and means operatively coupling the motor means to the lead screw means so that when the motor means runs said lead screw means will turn in the internally threaded means to thereby move said support means.

4. The apparatus as in any of claims 1, 2 or 3 wherein said image receptor is a radiographic film that is coincident with said imaging plane.

5. The apparatus in any of claims 1, 2 or 3 including:

a member projecting from said image receptor carriage and extending away from said imaging plane, said one end of said link means being pivotally connected to said member as aforesaid at a location that is at a fixed distance from said film plane.

6. Diagnostic x-ray table apparatus comprising means for performing tomography and other x-ray procedures and having a base, an x-ray transmissive table top supported from the base, a column extending above and below the table top and mounted for moving longitudinally of said top, means for moving the column, carriage means for an image receptor having an imaging plane, said carriage means mounted below the table top for moving longitudinally of said top, x-ray tube means and means supporting said tube means from said column for angulation of said tube means about an axis extending laterally of the table top substantially perpendicular to the plane of column movement, said means for performing tomography including:

arm means having a lower end region pivotally connected to said image receptor carriage for pivoting on laterally extending axis coincident with said imaging plane, means for coupling an upper end region of said arm means to said x-ray tube means for sliding relative thereto causing said arm means and x-ray tube means to angulate together about said laterally extending tube means angulation axis in response to longitudinal movement of said column so that the central ray of the x-ray beam will always be parallel to said arm means and directed at the same point on said imaging plane and on the plane that is to be imaged in a body on the table top as the column is translated longitudinally during tomography, extensible and contractible link means and support means below the table top on which said link means is mounted for pivoting about a laterally extending axis, one end region of said link means on one side of said axis being pivotally connected to said receptor carriage means and another end region on the other side of said axis being pivotally connected to said movable column substantially below said table top, longitudinal movement of said column in one direction causing the common angulation axis for said arm and x-ray tube means above the table top on the column to move in parallelism with the axis on which said link means is pivotally connected to the column to thereby cause said arm means and link means to pivot coordinately and move said receptor means and its imaging plane in the opposite direction, such that said arm means pivots about a fixed virtual axis above tne table top that is coincident with the plane in the body that is to be imaged and the distance from said imaged plane to said imaging plane is proportional to the distance between said link means pivot axis and said imaging plane.

7. The apparatus as in claim 6 including means for adjusting said support means for moving the pivot axis for said link means selectively toward or away from said imaging plane to thereby establish said virtual axis for said arm means at corresponding selected image planes in a body.

8. The apparatus as in any of claims 6 or 7 including a member extending downwardly from said receptor carriage and said pivotal connection between said one end region of said link means and said carriage being made on said member at a distance below said imaging plane in the receptor.

9. The apparatus as in any of claims 6 or 7 wherein said arm means comprises a straight bar and said coupling means comprises a guide member attached to said x-ray tube means for rotating therewith on a common axis, said bar means being engaged with said member for sliding therein.

* * * * *